United States Patent

Jacober et al.

Patent Number: 5,704,941
Date of Patent: Jan. 6, 1998

[54] TIBIAL PREPARATION APPARATUS AND METHOD

[75] Inventors: John S. Jacober, Oakland; Andrij J. Nedilsky, Westwood; Kenneth H. Trimmer, Waldwick; Thomas G. Wilson, West Milford, all of N.J.

[73] Assignee: Osteonics Corp., Allendale, N.J.

[21] Appl. No.: 552,594

[22] Filed: Nov. 3, 1995

[51] Int. Cl.$^6$ .................................................. A61B 17/56
[52] U.S. Cl. .................................. 606/88; 606/87
[58] Field of Search .................................. 606/86, 87, 88, 606/59; 623/20; 411/348

[56] References Cited

U.S. PATENT DOCUMENTS

| | | | |
|---|---|---|---|
| 3,596,554 | 8/1971 | Low | 411/348 |
| 5,282,803 | 2/1994 | Lackey | 606/80 |
| 5,462,550 | 10/1995 | Dietz et al. | 606/86 |

OTHER PUBLICATIONS

The P.C.A Primary Total Knee System, Howmedica Inc., 1984.
Duracon® The Tibial System, Howmedica, pp. 12–15, 1994.

*Primary Examiner*—Michael Buiz
*Assistant Examiner*—David O. Reip
*Attorney, Agent, or Firm*—Arthur Jacob

[57] ABSTRACT

Apparatus and method for the preparation of the proximal tibia for resection at a selected resection level utilize an external alignment shaft having an exposed upper end for the reception of a tibial resection guide over the exposed upper end for movement downwardly along the alignment shaft, securement to the alignment shaft at a resection location along the alignment shaft, and affixation to the proximal tibia at the resection level, the alignment shaft having an upper rod detachable from a lower tubular member for withdrawal of the upper rod from the lower tubular member, and for withdrawal upwardly from the tibial resection guide while the tibial resection guide is maintained affixed to the proximal tibia at the resection location, for full access of the tibial resection guide to a resection device to accomplish resection of the proximal tibia. A head at the upper end of the alignment shaft is anchored to the proximal tibia with fixation pins mounted for movement relative to the head for facilitating advancement and retraction of the fixation pins without disturbing the location of the tibial resection guide. The tibial resection guide is coupled to the alignment shaft with a securing member which projects sideways from the tibial resection guide so as to facilitate access to the tibial resection guide by the resection device. Selective attachment and detachment of a stylus assembly and the tibial resection guide is facilitated by a quick-connect mechanism, which assures positive location of a stylus for accurate location of the resection level.

27 Claims, 8 Drawing Sheets

TIBIAL PREPARATION APPARATUS AND METHOD

The present invention relates generally to the implant of prosthetic joints and pertains, more specifically, to the preparation of the proximal tibia for the implant of a tibial knee prosthesis. In particular, instrumentation and method are provided for location and alignment of the proximal cut of the tibia.

A wide variety of instruments have been made available for attaining the appropriate location and orientation of the proximal cut of the tibia for the implant of the tibial component of a knee prosthesis. In short, these instruments locate a tibial resection guide, with the aid of either extramedullary or intramedullary alignment members, for affixation to the proximal tibia to provide a guide for a cutting device, such as a saw blade, which makes the proximal cut of the tibia at a selected resection level.

The present invention provides apparatus and method which utilize an extramedullary alignment shaft for locating the tibial resection guide with greater ease and increased accuracy, and enabling relatively uninhibited access to the tibial resection guide, once the tibial resection guide is located appropriately at a resection location, for the accomplishment of the desired proximal cut. As such, the present invention attains several objects and advantages, some of which are summarized as follows: Enables increased accuracy, with ease, by allowing the independent setting of each alignment variable during placement and alignment of an external alignment member, prior to coupling a tibial resection guide with the external alignment member at an appropriate resection location; facilitates the location and affixation of the tibial resection guide at the desired resection location after independent accurate alignment of the external alignment member relative to the tibia; enables the removal of the external alignment member, subsequent to affixation of the tibial resection guide at the resection location, with minimal to no disruption of the alignment of the tibial resection guide at the resection location, to provide uninhibited access to the tibial resection guide for accomplishing the proximal cut at the selected resection level; provides an arrangement of component parts which reduces the potential for impeded operation of the resection device as the resection device is guided through the proximal cut of the tibia; facilitates selective attachment and detachment of component parts of the instrument system for increased ease of use and concomitant decreased time in the operating room, to the benefit of both the patient and the surgeon; provides an ergonomically more effective instrument system for reducing complexity and increasing the ease with which more accurate results are attained; enables a quicker and more accurate implant procedure with less invasive techniques; and provides a more practical and economical construction which is rugged enough to withstand the rigors of use over a relatively long service life, with the preservation of accuracy and ease of use.

The above objects and advantages, as well as further objects and advantages, are attained by the present invention which may be described briefly as an improvement in an apparatus used in connection with the implant of a prosthetic knee implant wherein the proximal tibia of a tibia is prepared for resection at a selected resection level for the reception of a tibial component of the prosthetic knee implant, the proximal tibia having a tibial eminence, the improvement comprising: an external alignment shaft including an upper segment and a lower segment located along a common alignment axis, the upper segment being selectively movable along the alignment axis relative to the lower segment and having an exposed upper end; a head at the exposed upper end of the upper segment, the head extending rearwardly for placement over the tibial eminence when the alignment shaft is located forward of the tibia; anchoring means on the head for anchoring the head to the proximal tibia with the alignment shaft located forward of the tibia; clamping means on the alignment shaft for clamping the upper segment and the lower segment of the alignment shaft against movement relative to one another subsequent to anchoring of the head to the proximal tibia; alignment means for aligning the alignment shaft relative to the tibia subsequent to anchoring the head to the proximal tibia; a tibial resection guide having coupling means for placement over the exposed upper end of the upper segment of the alignment shaft, from above the exposed upper end, to engage the tibial resection guide with the upper segment and enable movement of the tibial resection guide downwardly, over the exposed upper end, along the upper segment, subsequent to anchoring the head to the proximal tibia; a stylus assembly having attachment means for attaching the stylus assembly to the tibial resection guide for movement with the tibial resection guide along the upper segment, the stylus assembly including a stylus engageable with the proximal tibia to locate the tibial resection guide at a resection location wherein the tibial resection guide is located for guiding resection at the selected resection level; the coupling means of the tibial resection guide including securing means for selectively securing the tibial resection guide against movement along the upper segment when the tibial resection guide is located at the resection location; and affixation means for affixing the tibial resection guide to the proximal tibia when the tibial resection guide is located at the resection location; the securing means of the coupling means of the tibial resection guide being selectively releasable for releasing the securement between the tibial resection guide and the upper segment of the alignment shaft, subsequent to affixation of the tibial resection guide to the proximal tibia, and the clamping means of the alignment shaft being selectively releasable for releasing the upper segment of the alignment shaft for movement relative to the lower segment, subsequent to the affixation of the tibial resection guide, to enable withdrawal of the upper segment from the tibial resection guide and provide uninhibited access to the tibial resection guide for accomplishing resection at the selected resection level.

In addition, the invention includes an improvement in a method for implanting a prosthetic knee implant wherein the proximal tibia of a tibia is prepared for resection at a selected resection level for the reception of a tibial component of the prosthetic knee implant, the proximal tibia having a tibial eminence, the improvement comprising: locating an external alignment shaft having an upper segment and a lower segment, forward of the tibia, the upper segment being selectively movable along an alignment axis relative to the lower segment and having an exposed upper end and a head at the exposed upper end of the upper segment, with the head extending rearwardly relative to the tibia; placing the head over the tibial eminence when the alignment shaft is located forward of the tibia; anchoring the head to the proximal tibia with anchoring means, with the alignment shaft located forward of the tibia; clamping the upper segment and the lower segment of the alignment shaft against movement relative to one another subsequent to anchoring of the head to the proximal tibia; aligning the alignment shaft relative to the tibia subsequent to anchoring the head to the proximal tibia; placing a tibial resection guide having coupling means over the exposed upper end of the upper segment of the alignment shaft, from above the exposed upper end, to engage the tibial resection guide with the upper segment and enable movement of the tibial resection guide downwardly, over the exposed upper end, along the upper segment, subsequent to anchoring the head to the proximal tibia; attaching a stylus assembly to the tibial resection guide for movement with the tibial resection guide along the upper segment, the stylus assembly including a stylus, and engaging the stylus with the proximal tibia to locate the tibial resection guide at a resection location wherein the tibial resection guide is located for resection at the selected resection level; securing the tibial resection guide against movement along the upper segment when the tibial resection guide is located at the resection location; affixing the tibial resection guide to the proximal tibia when the tibial resection guide is located at the resection location; releasing the securement between the tibial resection guide and the upper segment of the alignment shaft, subsequent to affixation of the tibial resection guide to the proximal tibia; releasing the upper segment of the alignment shaft for movement relative to the lower segment, subsequent to the affixation of the tibial resection guide; and withdrawing the upper segment from the tibial resection guide to provide uninhibited access to the tibial resection guide for accomplishing resection at the selected resection level.

Further, the invention includes an improvement in an apparatus used in connection with the implant of a prosthetic knee implant wherein the proximal tibia of a tibia is prepared for resection for the reception of a tibial component of the prosthetic knee implant, the proximal tibia having a tibial eminence, the improvement comprising: an external alignment shaft having an upper end; a head at the upper end of the external alignment shaft, the head extending rearwardly for placement over the tibial eminence when the alignment shaft is located forward of the tibia; and anchoring means on the head for anchoring the head to the proximal tibia with the alignment shaft located forward of the tibia; the anchoring means including a first fixation pin for anchoring the head against anterior and posterior movements relative to the tibia, and a second fixation pin for anchoring the head against rotation about the first fixation pin, at least one of the first and second fixation pins being mounted in the head for selective movement in upward and downward directions relative to the head, between an advanced position wherein the moveable fixation pin extends downwardly from the head for extending into the proximal tibia, and a retracted position wherein the moveable fixation pin is retracted from the proximal tibia to enable selective release of the moveable fixation pin from the proximal tibia while the head remains in place over the tibial eminence.

Still further, the invention includes an improvement in an apparatus used in connection with the implant of a prosthetic knee implant wherein the proximal tibia of a tibia is prepared for resection for the reception of a tibial component of the prosthetic knee implant, the proximal tibia having a tibial eminence, the improvement comprising: an external alignment shaft having an upper end; a head at the upper end of the external alignment shaft, the head extending rearwardly for placement over the tibial eminence when the alignment shaft is located forward of the tibia; and anchoring means on the head for anchoring the head to the proximal tibia with the alignment shaft located forward of the tibia, the anchoring means including: a first fixation pin mounted in the head for selective movement in upward and downward directions relative to the head between an advanced position wherein the first fixation pin extends downwardly from the head for extending into the proximal tibia to anchor the head to the proximal tibia against upward movement of the head, and the alignment shaft, away from the proximal tibia, and a retracted position wherein the first fixation pin is retracted from the proximal tibia to release the head, and the alignment shaft, for upward movement relative to the proximal tibia; and a second fixation pin mounted in the head for selective movement in upward and downward directions relative to the head between an advanced position wherein the second fixation pin extends downwardly from the head for extending into the proximal tibia to anchor the head to the proximal tibia against upward movement of the head, and the alignment shaft, away from the proximal tibia, and a retracted position wherein the second fixation pin is retracted from the proximal tibia to release the head, and the alignment shaft, for upward movement relative to the proximal tibia; the first and second fixation pins being spaced from one another such that upon movement of both the first and second fixation pins to the respective advanced positions, rotation of the head about one of the first and second pins is precluded; and upon movement of both the first and second fixation pins to the respective retracted positions, the fixation pins are retracted from the proximal tibia to enable selective release of the fixation pins from the proximal tibia while the head remains in place over the tibial eminence.

Additionally, the invention includes an improvement in an apparatus used in connection with the implant of a prosthetic joint wherein the bone of the natural joint is prepared for resection at a selected resection location for the reception of a component of the prosthetic joint, the improvement comprising: an alignment shaft for anchoring to the bone of the natural joint, the alignment shaft having an alignment axis; and a resection guide having coupling means for placement over the alignment shaft to engage the resection guide with the alignment shaft and enable movement of the resection guide along the alignment shaft to locate the resection guide at the resection location wherein the resection guide is located for guiding resection of the bone; the coupling means of the resection guide including securing means for selectively securing the resection guide against movement along the alignment shaft when the resection guide is located at the resection location; the alignment shaft including an outer surface having opposite side edges and a portion having a wedge-shaped surface contour configuration transverse to the alignment axis and tapered toward at least one of the opposite side edges; and the securing means of the coupling means of the resection guide including an inner surface having a portion generally complementary to the surface contour configuration of the portion of the outer surface of the alignment shaft, and a securing member including an operator element extending in a sideways direction from the resection guide for selectively engaging the complementary portions of the inner surface and the outer surface to secure the resection guide upon the alignment shaft at the resection location.

The invention further includes an improvement in an apparatus used in connection with the implant of a prosthetic knee implant wherein the proximal tibia of a tibia is prepared for resection at a selected resection level for the reception of a tibial component of the prosthetic knee implant, the proximal tibia having a tibial eminence, the improvement comprising: an external alignment shaft for anchoring to the tibia; a tibial resection guide having coupling means for placement upon the alignment shaft to engage the tibial resection guide with the alignment shaft and enable movement of the tibial resection guide along the alignment shaft, subsequent to anchoring the alignment shaft to the tibia; and a stylus assembly having attachment means for attaching the stylus assembly to the tibial resection guide for movement with the tibial resection guide along the alignment shaft, the stylus assembly including a stylus engageable with the proximal tibia to locate the tibial resection guide at a resection location wherein the tibial resection guide is located for guiding resection at the selected resection level; the attachment means for attaching the stylus assembly to the tibial resection guide comprising a quick-connect mechanism including an elongate socket extending downwardly into the tibial resection guide, an elongate plug on the stylus assembly, the plug being complementary to the socket and extending in the downward direction, a recess in the tibial resection guide, the recess communicating with the socket and extending transverse to the socket, a projection mounted in the plug for movement in transverse directions between an extended position, wherein the projection engages the recess to secure the plug in the socket, and a retracted position, wherein the projection is released from the recess to release the plug from the socket, and actuator means for selectively moving the projection between the advanced and retracted positions thereof.

The invention further includes an improvement in a method used in connection with the implant of a prosthetic knee implant wherein the proximal tibia of a tibia is prepared for resection at a selected resection level for the reception of a tibial component of the prosthetic knee implant, the proximal tibia having a tibial eminence, the improvement comprising: locating an external alignment shaft forward of the tibia, the external alignment shaft having an upper end, and a head at the upper end of the external alignment shaft, the head extending rearwardly for placement over the tibial eminence when the alignment shaft is located forward of the tibia; and anchoring the head to the proximal tibia with anchoring means, with the alignment shaft located forward of the tibia, the anchoring means including a first fixation pin for anchoring the head against anterior and posterior movements relative to the tibia, and a second fixation pin for anchoring the head against rotation about the first fixation pin, at least one of the first and second fixation pins being mounted in the head for selective movement in upward and downward directions relative to the head, between an advanced position wherein the moveable fixation pin extends downwardly from the head for extending into the proximal tibia, and a retracted position wherein the moveable fixation pin is retracted from the proximal tibia, the improvement including advancing one of the first and second fixation pins into the proximal tibia to first anchor the head to the proximal tibia against anterior and posterior movements relative to the proximal tibia, with the head seated upon the proximal tibia, and subsequently advancing the other of the first and second fixation pins into the proximal tibia to anchor the head against rotational movement about the said one of the first and second fixation pins.

The invention will be understood more fully, while still further objects and advantages will become apparent, in the following detailed description of preferred embodiments of the invention illustrated in the accompanying drawing, in which.

Figure 1:
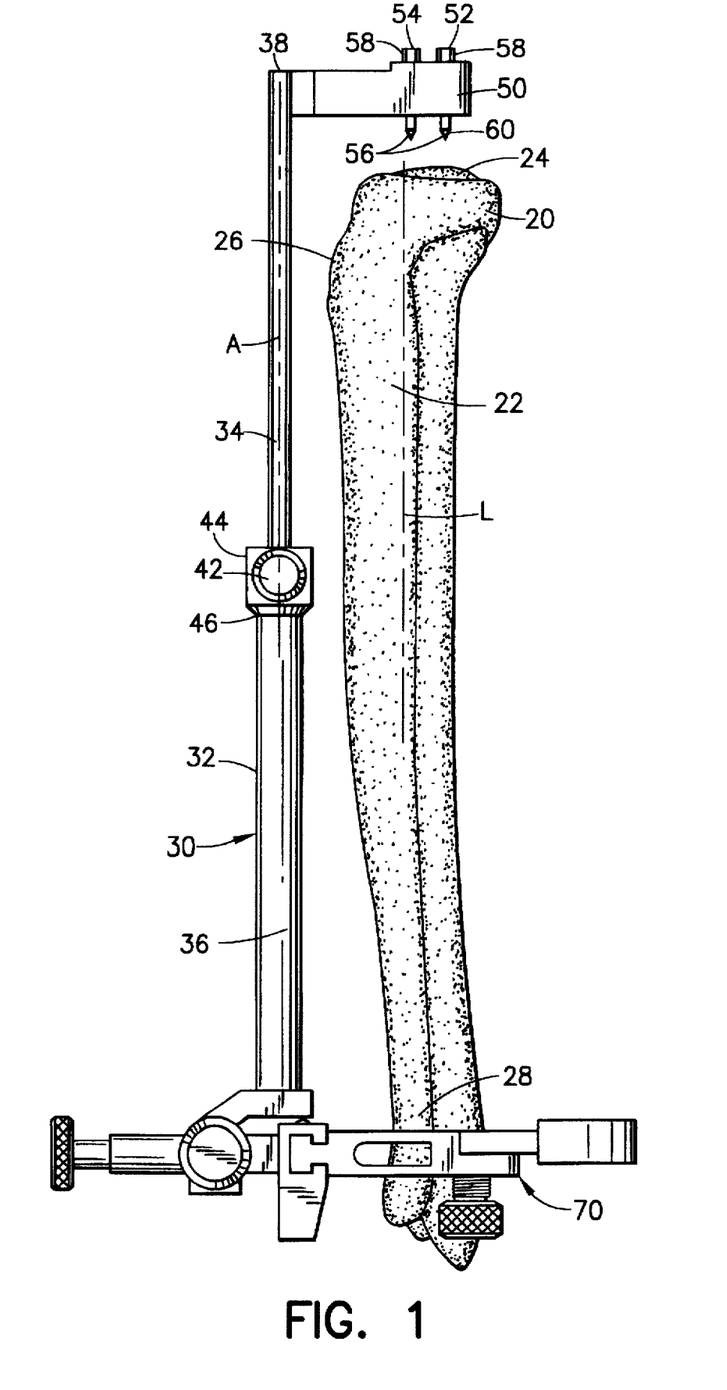
FIG. 1 is a side elevational view showing initial placement of an apparatus constructed in accordance with the present invention, along the tibia in accordance with method of the present invention.

Referring now to the drawing, and especially to FIG. 1 thereof, the proximal tibia 20 of a tibia 22 includes a tibial eminence 24 and an anterior cortex 26 and is to be prepared for the reception of the tibial component of a prosthetic knee implant (not shown) by resection of the proximal tibia 20. Tibia 22 includes a long axis L and a distal tibia 28. Apparatus constructed in accordance with the invention for the preparation of the proximal tibia 20 is illustrated generally at 30 and is seen to include an external alignment shaft 32 having an upper segment in the form of a rod 34 and a lower segment in the form of a tubular member 36. Rod 34 includes an upper end 38 and a lower end 40 (see FIG. 11) and is to be received within tubular member 36 in telescoping engagement adjacent the lower end 40, for selective movement relative to the tubular member 36 along a common alignment axis A. Clamping means, shown in the form of a thumbscrew 42 threaded through a collar 44 integral with the tubular member 36 at the upper end 46 of the tubular member 36, selectively clamps the rod 34 in place at any location of rod 34 along alignment axis A relative to tubular member 36, when the rod 34 is telescoped into the tubular member 36.

Figure 2:
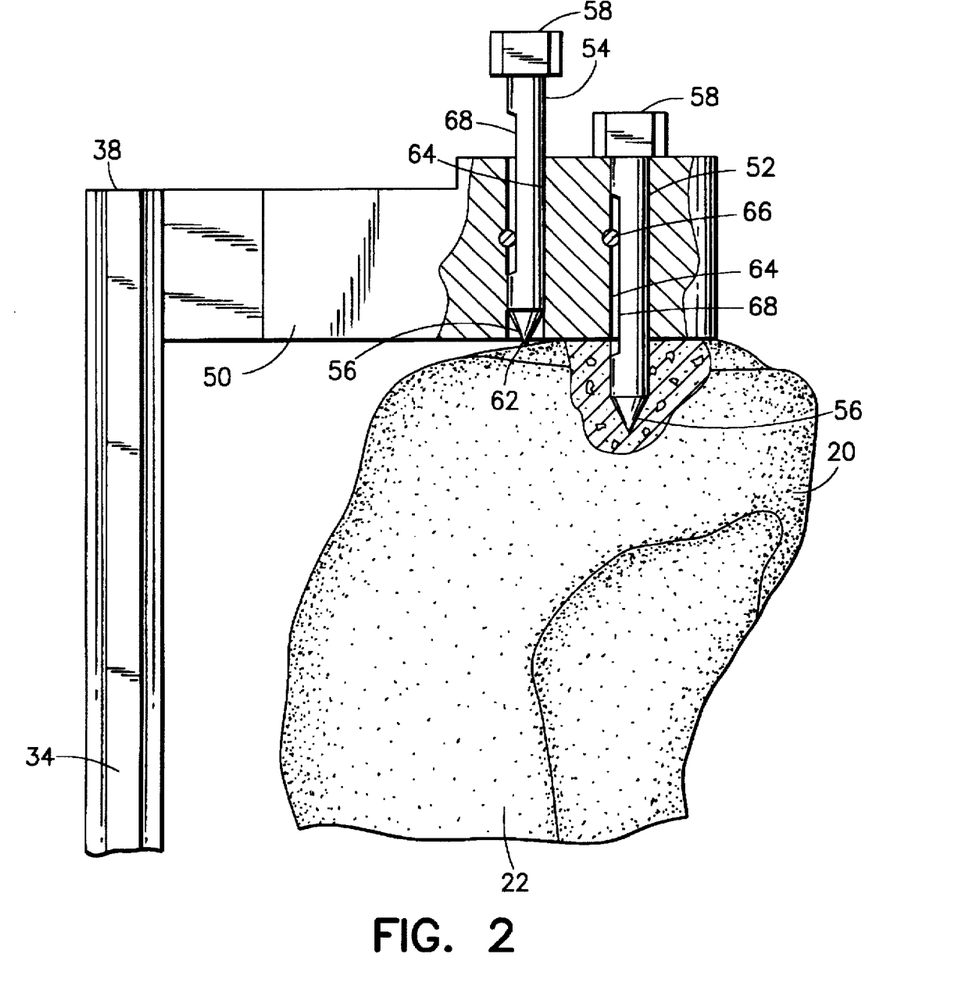
FIG. 2 is an enlarged fragmentary view of a portion of FIG. 1, partially broken away, and with component parts shown in another position.
Figure 3:
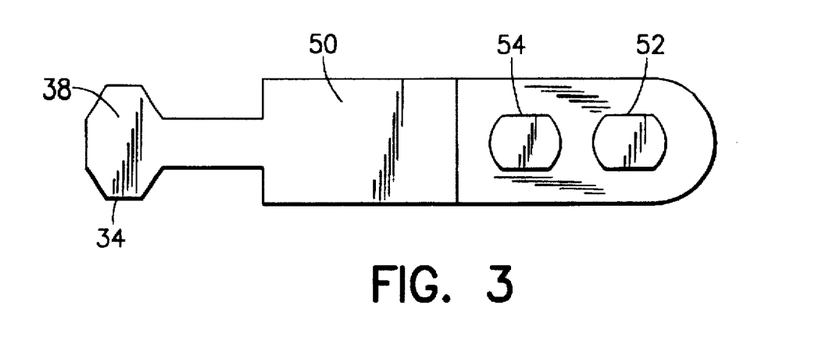
FIG. 3 is a fragmentary plan view of a portion of component parts illustrated in FIG. 2.
Figure 4:
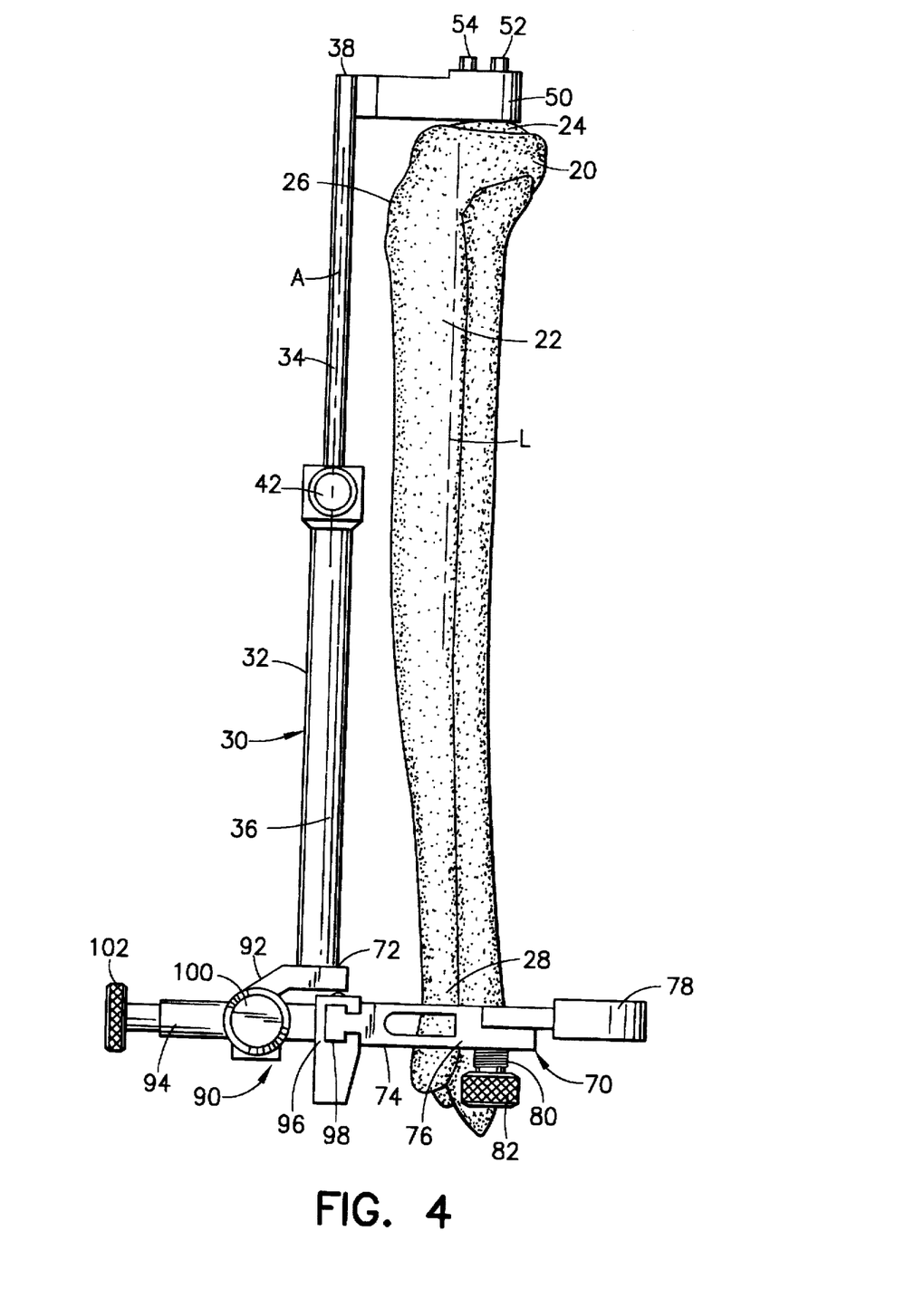
FIG. 4 is a side elevational view similar to FIG. 1, but with the apparatus fully in place along the tibia.
Figure 5:
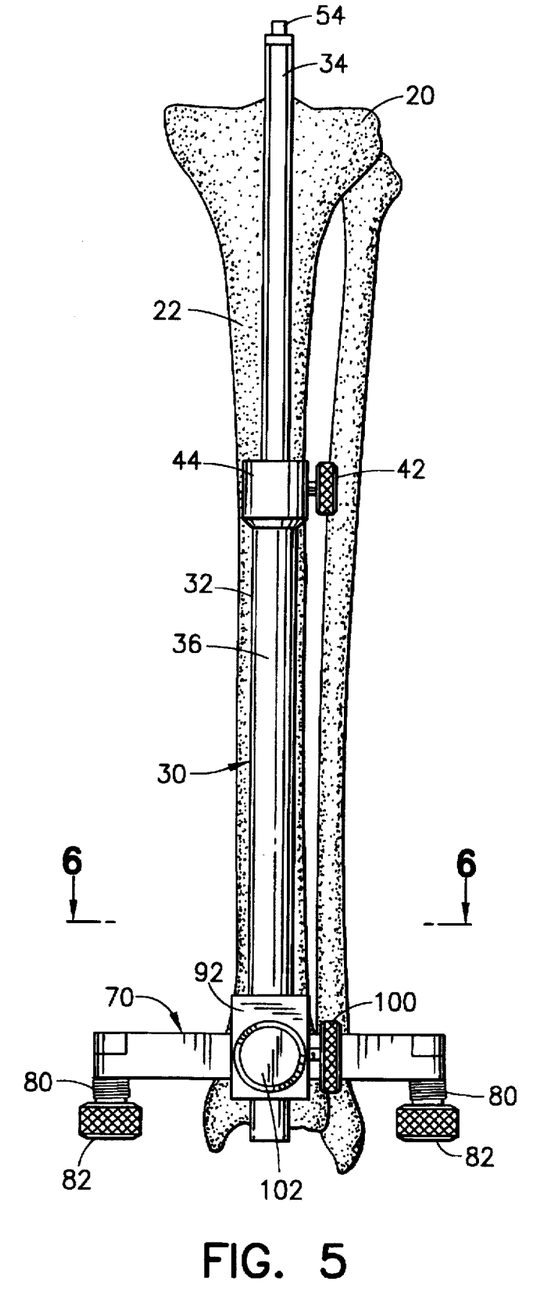
FIG. 5 is a front elevational view of the apparatus fully in place along the tibia.
Figure 6:
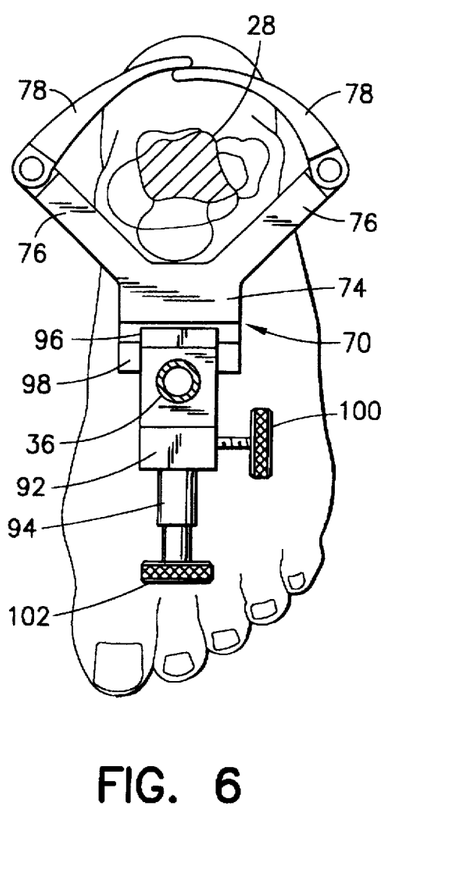
FIG. 6 is a transverse cross-sectional view taken along line 6—6 of FIG. 5.

A head 50 is integral with the rod 34 and extends rearwardly, in the posterior direction, from the upper end 38 of rod 34. Head 50 carries anchoring means in the form of a first fixation pin 52 and a second fixation pin 54. Each fixation pin 52 and 54 includes a pointed lower end 56 and a headed upper end 58 and is mounted in the head 50 for sliding movement in upward and downward directions, relative to the head 50, between a lower, advanced position, wherein the pointed lower end 56 extends downwardly from the head 50, as seen at 60 in FIG. 1, and an upper, retracted position, wherein the pointed lower end 56 is retracted into the head 50, as seen at 62 in FIG. 2. As best seen in FIG. 2, mounting means places each fixation pin 52 and 54 within a complementary bore 64 in the head 50, captured for sliding movement between the advanced and retracted positions by means of a peg 66 fixed in the head 50 and passing through a groove 68 in each fixation pin 52 and 54. In the preferred arrangement, fixation pins 52 and 54 are aligned in frontto-back arrangement, with first fixation pin 52 located behind, or spaced posterior of, second fixation pin 54.

Turning now to FIGS. 2 through 6, as well as to FIG. 1, a lower clamp 70 is mounted at the lower end 72 of the tubular member 36 and includes a yoke 74 having diverging arms 76 and a jaw 78 journaled upon each arm 76. Lower clamp 70 is placed around the distal tibia 28, just above the malleoli, and the jaws 78 are biased into a closed, clamping configuration by springs 80, thereby locating the lower end 72 of the tubular member 36 and, consequently, the lower end of the alignment shaft 32, in alignment with the distal tibia 28, forward of the distal tibia 28. The biasing force of springs 80 is adjustable by virtue of knobs 82 which can be moved to selectively increase or decrease the force exerted by springs 80 on the respective jaws 78.

Rod 34 then is telescoped downwardly within tubular member 36 until head 50 is seated upon proximal tibia 20, placed over the tibial eminence 24 and located such that the rod 34 is forward of the anterior cortex 26 of the proximal tibia 20. The fixation pins 52 and 54 then are centered over the tibial eminence 24 and the most posterior fixation pin 52 is pushed downwardly into the advanced position to enter the proximal tibia 20 and anchor the head 50 against anterior and posterior movements relative to the proximal tibia 20. Then, rotation is adjusted by rotating the head 50 about the advanced fixation pin 52 to align the upper end 38 of the rod 34 with the tibia 22, and the most anterior fixation pin 54 is pushed downwardly into the advanced position to enter the proximal tibia 20 and anchor the head 50 against rotation relative to the proximal tibia 20. Thumbscrew 42 then is tightened to clamp rod 34 against further movement relative to tubular member 36.

Alignment means is shown in the form of an alignment assembly 90 which includes a first carriage 92 integral with the lower end 72 of the tubular member 36 and mounted for sliding movement along a first guideway 94 which, in turn, is carried by a second carriage 96 mounted for sliding movement along a second guideway 98 integral with the yoke 74 of clamp 70. The first guideway 94 has a rectangular cross-sectional configuration and extends in an anterior-posterior direction for enabling the first carriage 92 to be moved selectively along the first guideway 94 in anterior and posterior directions so as to align axis A of the alignment shaft 32 appropriately with the long axis L of the tibia 22, in the anterior and posterior directions. The second guideway 98 has a T-shaped cross-sectional configuration and extends in a medial-lateral direction for enabling the second carriage 96 to be moved selectively along the second guideway 98 in medial and lateral directions so as to align axis A of the alignment shaft 32 appropriately with the long axis L of the tibia 22, in the medial and lateral directions. Once the axis A is aligned as described, a first thumbscrew 100 in the first carriage 92 is tightened to secure the first carriage 92 in place on the first guideway 94, and a second thumbscrew 102 in the second carriage 96 is tightened to secure the second carriage 96 in place on the second guideway 98.

Turning now to FIGS. 7 through 10, a tibial resection guide 110 is to be assembled with the alignment shaft 32 and located at an appropriate resection location for the accomplishment of the desired proximal cut along the proximal tibia 20. To that end, tibial resection guide 110 includes a cutting guide surface, shown in the form of a saw blade guide slot 112 extending in a medial-lateral direction between the sides of the tibial resection guide 110 and through the tibial resection guide 110 in the anterior-posterior direction. A plurality of holes 114 also extend through the tibial resection guide 110 in the anterior-posterior direction.

Figure 7:
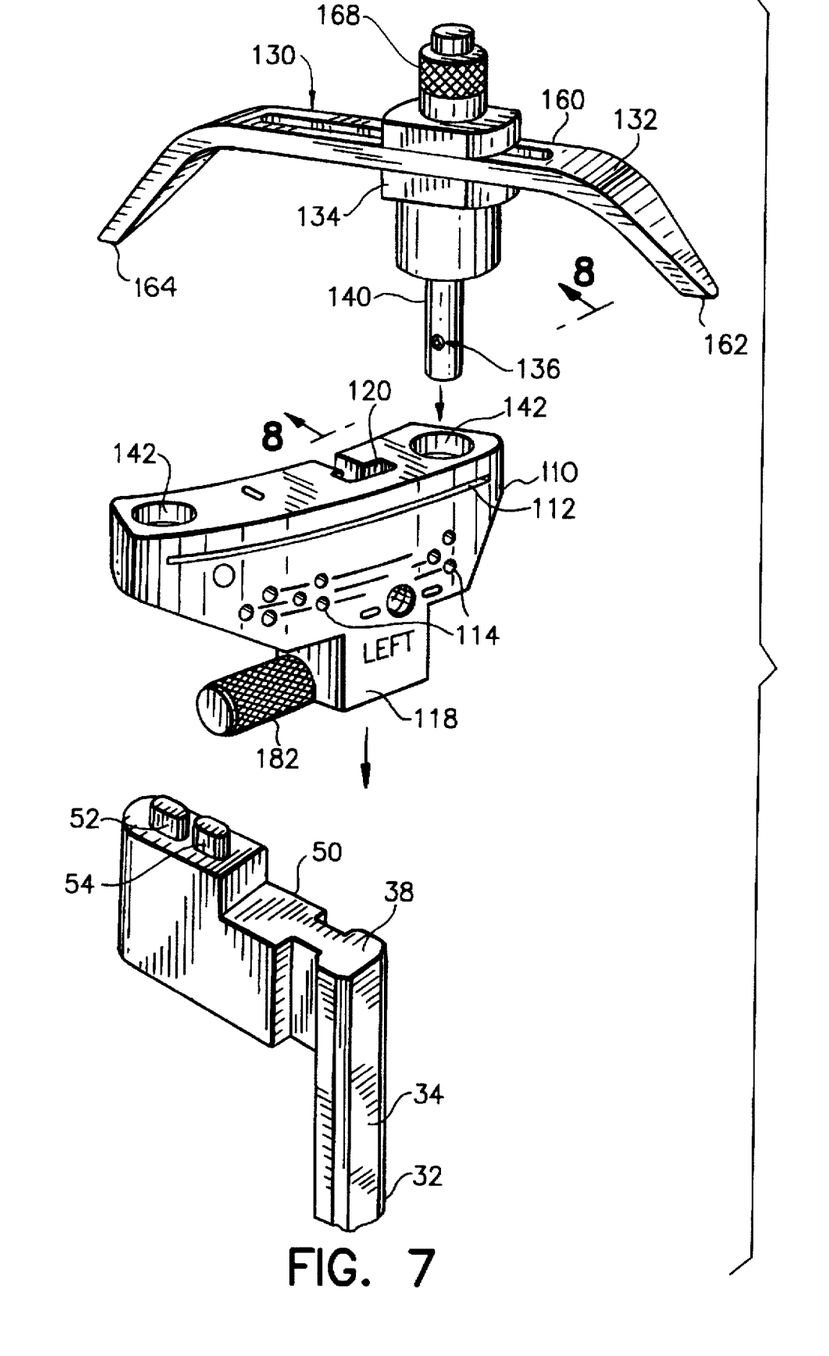
FIG. 7 is an exploded perspective view of a tibial resection guide and stylus assembly of the apparatus about to be placed over the exposed upper end of the alignment shaft of the apparatus.
Figure 8:
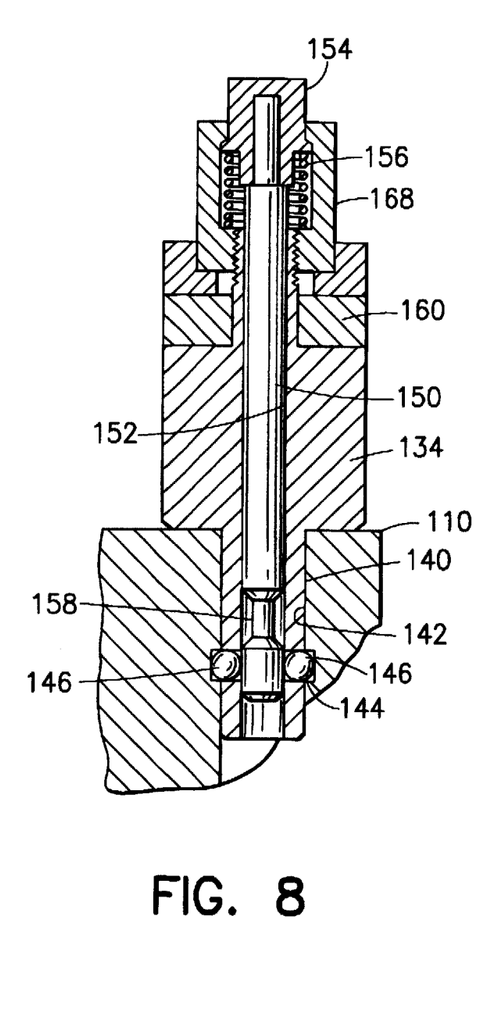
FIG. 8 is an enlarged cross-sectional view taken along line 8—8 of FIG. 7, with the stylus assembly attached to the tibial resection guide.

In order to assemble the tibial resection guide 110 with the alignment shaft 32, the tibial resection guide 110 is provided with coupling means including a depending sleeve-like extension 118 of the tibial resection guide 110 and a channel 120 passing through the tibial resection guide 110, and the extension 118 thereof, in the direction parallel to the alignment axis A of the alignment shaft 32 and having an inner surface 122 with a contour configuration generally complementary to the contour configuration of outer surface 124 of the rod 34 of the alignment shaft 32, at the upper end 38 of the rod 34. Accordingly, the coupling means of the tibial resection guide 110 is placed over the exposed upper end 38 of the rod 34, from above the exposed upper end 38, as illustrated in FIG. 7, with the upper end 38 of the rod 34 slipped into the channel 120 of the tibial resection guide 110, enabling the tibial resection guide 110 to be moved downwardly along the rod 34 until the tibial resection guide 110 is located at the appropriate resection location. The ability to place the tibial resection guide 110 upon the alignment shaft 32, over the top of the alignment shaft 32, subsequent to attaching the alignment shaft 32 along the tibia 22, rather than requiring that the tibial resection guide 110 be assembled with the alignment shaft 32 prior to attachment and alignment of the alignment shaft 32 with the tibia 22, facilitates the appropriate alignment of the alignment shaft 32 and the accurate placement of the tibial resection guide 110 at the resection location, thereby reducing the time required to accomplish an accurate result, to the benefit of the patient and the surgeon.

The resection location of the tibial resection guide 110 is determined by a stylus assembly 130 which is most conveniently attached to the tibial resection guide 110 prior to placement of the tibial resection guide 110 on the rod 34. Stylus assembly 130 includes a tibial stylus 132 mounted upon a stylus housing 134 and is selectively attached to and detached from the tibial resection guide 110 by attachment means shown in the form of a quick-connect mechanism 136. Quick-connect mechanism 136 includes an elongate plug 140 projecting downwardly from the stylus housing 134 to be received within a selected one of two complementary elongate sockets 142 extending downwardly into the tibial resection guide 110, the tibial resection guide 110 being provided with one elongate socket 142 adjacent each side of the tibial resection guide 110. A recess in the form of an annular groove 144 in the tibial resection guide 110 communicates with the socket 142 and extends transverse to the socket 142 for the reception of a projection in the form of a ball 146 retained within the plug 140 and mounted in the plug 140 for movement between an extended position, wherein the ball 146 is in position to engage the groove 144 to secure the plug 140 within the socket 142, and a retracted position, wherein the ball is retracted into the plug 140 and out of the groove 144 to release the plug 140 from the socket 142. In the illustrated embodiment, diametrically opposed balls 146 engage groove 144 for enhanced securement.

Actuator means is shown in the form of a plunger 150 mounted for sliding movement within a bore 152 in the stylus housing 134 and including a pushbutton 154 affixed to the upper end of the plunger 150. The plunger 150 is coupled with the balls 146 so that upon placement of the plunger 150 in an upper position, as seen in FIG. 7, the balls 146 are moved to the extended positions thereof and engage the groove 144 to secure the stylus assembly 130 in place, attached to the tibial resection guide 110. A compression spring 156 biases the plunger 150 into the upper position thereof. Upon depression of the pushbutton 154, the plunger 150 is moved downwardly, against the bias of compression spring 156, thereby registering an annular recess 158 in the plunger 150 with the balls 146, enabling the balls 146 to move to the retracted position thereof, out of engagement with the groove 144, and the plug 140 is released for movement out of the socket 142.

Figure 9:
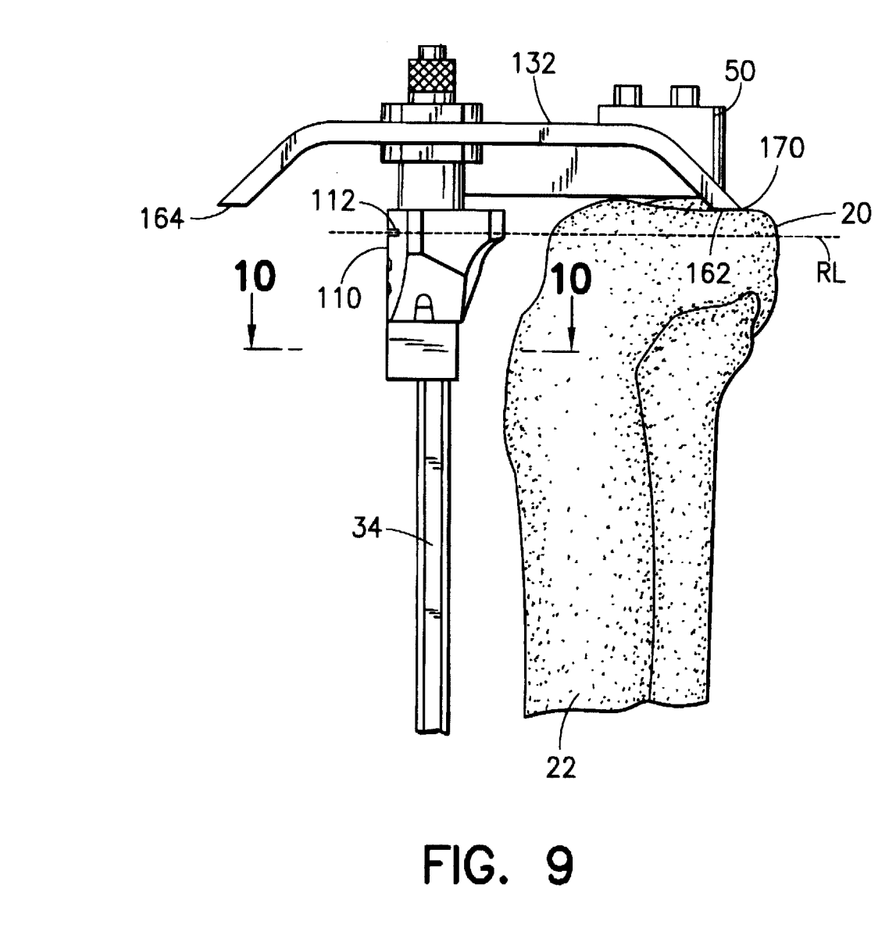
FIG. 9 is fragmentary side elevational view showing the tibial resection guide and stylus assembly in place upon the alignment shaft of the apparatus.

The tibial stylus 132 includes a slotted bar 160 and opposite stylus tips 162 and 164. The slotted bar 160 is clamped to the stylus housing 134 by a clamping member 166 secured by a clamping thumbnut 168, with either one of the stylus tips 162 or 164 placed in position to overlie the proximal tibia 20 when the tibial resection guide 110 is assembled with the alignment shaft 32, as described above. The slotted bar 160 enables selected anterior and posterior movements of the stylus 132 to locate the stylus tip 162, or the stylus tip 164, appropriately prior to clamping the stylus 132 in place in the stylus assembly 130. Thus, as seen in FIG. 9, the tibial resection guide 110 is moved downwardly along the rod 34 until the tip 162 of tibial stylus 132 engages the proximal tibia 20, along the tibial plateau 170, thereby placing the tibial resection guide 110 at the correct resection location for accomplishing the proximal cut at the desired resection level RL. The quick-connect mechanism 136 accomplishes a highly stable attachment of the stylus assembly 130 to the tibial resection guide 110 in a compact and easily operated arrangement. Thus, improved accuracy is attained in the location of the resection level RL, with a decrease in the time required for accomplishing accuracy, to the benefit of the patient and the surgeon.

The two stylus tips 162 and 164 are located at different elevations to enable the surgeon to choose one of two resection levels. In the examples provided in the illustrated embodiment, placement of the stylus tip 162 in position to engage the tibial plateau 170 locates the tibial resection guide 110, and the saw blade guide slot 112 thereof, in position to allow for a resection of 2 mm of bone below the elevation of the stylus tip 162. Alternately, placement of the stylus tip 164 in position to engage the tibial plateau 170 locates the tibial resection guide 110 in position to allow for a resection of 8 mm of bone below the elevation of the stylus tip 164.

Figures 10, 11:
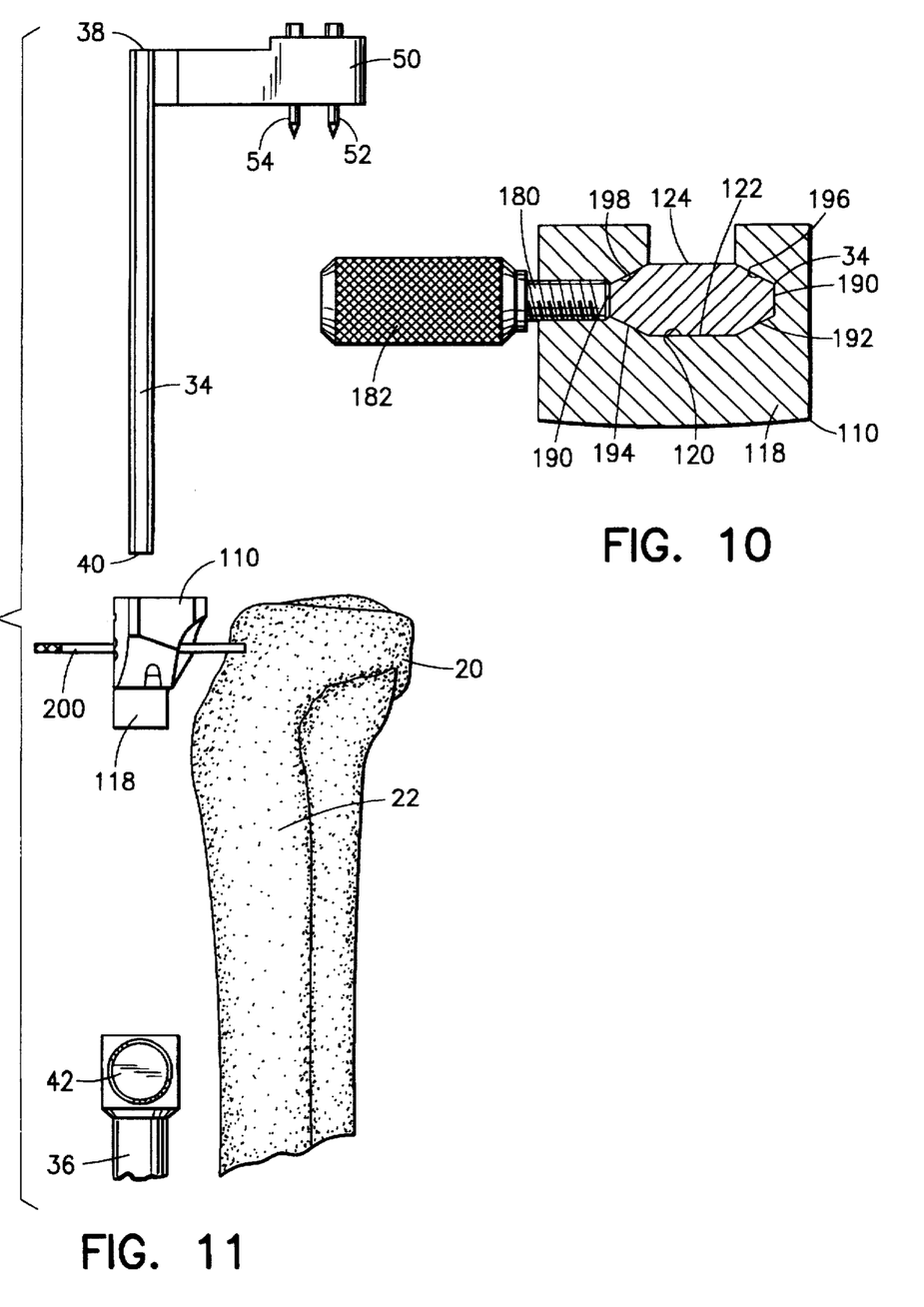
FIG. 10 is an enlarged cross-sectional view taken along line 10—10 of FIG. 9.
FIG. 11 is a fragmentary side elevational view showing the removal of a component part of the apparatus.

Once the tibial resection guide 110 is located at the resection location, securing means associated with the coupling means on the tibial resection guide 110 secure the tibial resection guide 110 to the rod 34 of the alignment shaft 32 to preclude further movement of the tibial resection guide 110 along the alignment shaft 32. As best seen in FIG. 10, the securing means includes a securing member in the form of a thumbscrew 180 threaded into the extension 118 of the tibial resection guide 110 to engage the rod 34 in the channel 120 and clamp the tibial resection guide 110 in place on the rod 34. A knob 182, which is the operator element of the thumbscrew 180, extends along a longitudinal axis aligned with the medial-lateral direction to project in a sideways direction from the extension 118, the knob 182 projecting in a medial-lateral direction from the medial side of the tibial resection guide 110. The placement of the thumbscrew 180, with the knob 182 projecting in the medial-lateral direction from the medial side of the tibial resection guide 110, assures that the knob 182 will be out of the way of the resection device when making the proximal cut, as explained below.

Effective operation of the securing means is assured, while enabling the sideways projection of the knob 182 of thumbscrew 180, by the particular contour configurations of the mating outer surface 124 of rod 34 and inner surface 122 of channel 120. Thus, the contour configuration of the outer surface 124 of rod 34 follows a double-wedge profile; that is, the outer surface 124 includes opposite side edges 190, a first portion 192 having a wedge-shaped surface contour configuration transverse to the alignment axis A and tapered toward one of the opposite side edges 190, and a second portion 194 having a wedge-shaped surface contour configuration transverse to the alignment axis A and tapered toward the other of the opposite side edges 190. The inner surface 122 of channel 120 follows a double-wedge profile generally complementary to the double-wedge profile of the outer surface 124 of rod 34 and includes a first portion 196 having a wedge-shaped surface contour configuration generally complementary to that of first portion 192, and a second portion 198 having a wedge-shaped surface contour configuration generally complementary to that of second portion 194.

When the thumbscrew 180 is tightened against a side edge 190 of the rod 34, the complementary first portions 192 and 196 are wedged together to establish a secure connection between the extension 118 of the tibial resection guide 110 and the rod 34. The purpose of the double-wedge profile is to provide the same wedging action in both a right and a left tibial resection guide, while maintaining the desired medial location of the thumbscrew. Thus, the illustrated tibial resection guide 110 is for use in connection with a left knee and the thumbscrew 180, which projects from the medial side of the extension 118, engages one side edge 190 of the rod 34 to wedge together the portions 192 and 196. In a similar tibial resection guide for use in connection with a right knee, the medial and lateral sides are the reverse of the illustrated tibial resection guide 110 and, in order to project from the medial side of the extension of the tibial resection guide, the corresponding thumbscrew would engage the opposite side edge 190 of the rod 34, thereby wedging together the portions 194 and 198 to secure the tibial resection guide in place on the rod 34. In this manner, alignment shaft 32, with rod 34 thereof, is available for use in connection with both a right knee and a left knee.

Figure 12:
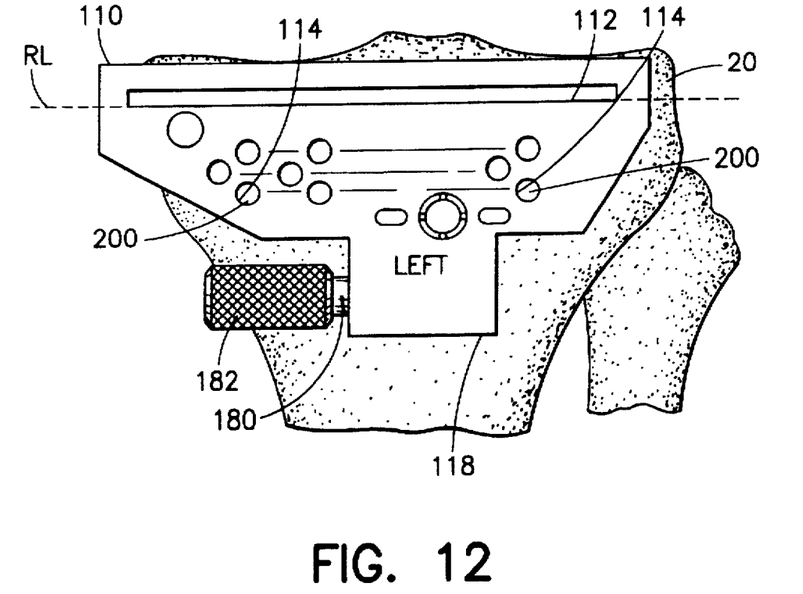
FIG. 12 is a fragmentary front elevational view showing the tibial resection guide in place at a resection location for resection of the proximal tibia.
Figure 13:
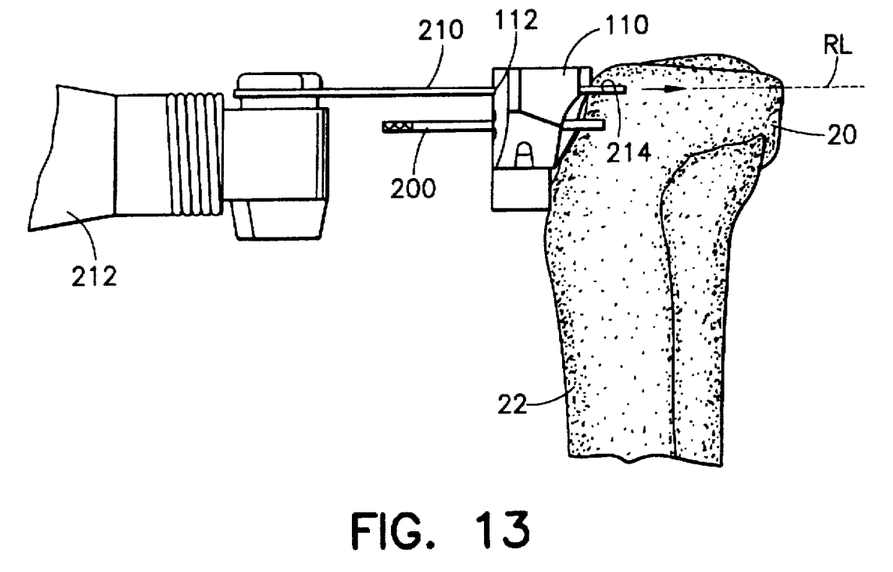
FIG. 13 is a fragmentary side elevational view showing resection of the proximal tibia.

Once the tibial resection guide 110 is located and secured to the alignment shaft 32 at the resection location, the stylus assembly 130 is detached from the tibial resection guide 110 by merely depressing the pushbutton 154 to release the plug 140 from the socket 142, as described above. As illustrated in FIGS. 11 and 12, the tibial resection guide 110 then is affixed to the proximal tibia 20 by affixation means, shown in the form of drill-pins 200 inserted through selected holes 114 in the tibial resection guide 110 and into the proximal tibia 20. Then, the thumbscrew 180 is loosened to release the securement of the tibial resection guide 110 on the rod 34, the thumbscrew 42 is loosened to release rod 34 for movement relative to tubular member 36, and the fixation pins 52 and 54 are extracted from the proximal tibia 20. The rod 34 then is removed by upward movement to withdraw the rod 34 from the tubular member 36 and from the tibial resection guide 110. It is noted that since the fixation pins 52 and 54 are mounted for sliding movement within the head 50, extraction of the fixation pins 52 and 54 is accomplished independent of any movement of head 50, and the orientation of the alignment shaft 32 remains undisturbed, thereby eliminating any concomitant forces which could dislodge the tibial resection guide 110 and disturb the placement and alignment of the tibial resection guide 110 at the resection location and, consequently, the alignment of the proximal cut. When the rod 34 is fully removed, the tibial resection guide 110 is moved along the drill-pins 200 in the posterior direction until the tibial resection guide 110 comes into contact with the proximal tibia 20, as seen in FIG. 13. The tibial resection guide 110 is fully exposed for uninhibited access to the tibial resection guide 110 and a saw blade 210 of a saw 212 then is inserted through the saw blade guide slot 112 to accomplish the proximal cut 214 at the resection level RL. Further, the knob 182 of thumbscrew 180 (see FIG. 12) is out of the way of saw 212, by virtue of the medial location of the thumbscrew 180 and the projection of the knob 182 in the medial-lateral direction.

It will be seen that the present invention attains the objects and advantages summarized above; namely: Enables increased accuracy, with ease, by allowing the independent setting of each alignment variable during placement and alignment of an external alignment member, prior to coupling a tibial resection guide with the external alignment member at an appropriate resection location; facilitates the location and affixation of the tibial resection guide at the desired resection location after independent accurate alignment of the external alignment member relative to the tibia; enables the removal of the external alignment member, subsequent to affixation of the tibial resection guide at the resection location, with minimal to no disruption of the alignment of the tibial resection guide at the resection location, to provide uninhibited access to the tibial resection guide for accomplishing the proximal cut at the selected resection level; provides an arrangement of component parts which reduces the potential for impeded operation of the resection device as the resection device is guided through the proximal cut of the tibia; facilitates selective attachment and detachment of component parts of the instrument system for increased ease of use and concomitant decreased time in the operating room, to the benefit of both the patient and the surgeon; provides an ergonomically more effective instrument system for reducing complexity and increasing the ease with which more accurate results are attained; enables a quicker and more accurate implant procedure with less invasive techniques; and provides a more practical and economical construction which is rugged enough to withstand the rigors of use over a relatively long service life, with the preservation of accuracy and ease of use.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. An improvement in an apparatus used in connection with the implant of a prosthetic knee implant wherein the proximal tibia of a tibia is prepared for resection at a selected resection level for the reception of a tibial component of the prosthetic knee implant, the proximal tibia having a tibial eminence, the improvement comprising:

an external alignment shaft including an upper segment and a lower segment located along a common alignment axis, the upper segment being selectively movable along the alignment axis relative to the lower segment and having an exposed upper end;

a head at the exposed upper end of the upper segment, the head extending rearwardly for placement over the tibial eminence when the alignment shaft is located forward of the tibia;

anchoring means on the head for anchoring the head to the proximal tibia with the alignment shaft located forward of the tibia;

clamping means on the alignment shaft for clamping the upper segment and the lower segment of the alignment shaft against movement relative to one another subsequent to anchoring of the head to the proximal tibia;

alignment means for aligning the alignment shaft relative to the tibia subsequent to anchoring the head to the proximal tibia;

a tibial resection guide having coupling means for placement over the exposed upper end of the upper segment of the alignment shaft, from above the exposed upper end, to engage the tibial resection guide with the upper segment and enable movement of the tibial resection guide downwardly, over the exposed upper end, along the upper segment, subsequent to anchoring the head to the proximal tibia;

a stylus assembly having attachment means for attaching the stylus assembly to the tibial resection guide for movement with the tibial resection guide along the upper segment, the stylus assembly including a stylus engageable with the proximal tibia to locate the tibial resection guide at a resection location wherein the tibial resection guide is located for guiding resection at the selected resection level;

the coupling means of the tibial resection guide including securing means for selectively securing the tibial resection guide against movement along the upper segment when the tibial resection guide is located at the resection location; and affixation means for affixing the tibial resection guide to the proximal tibia when the tibial resection guide is located at the resection location;

the securing means of the coupling means of the tibial resection guide being selectively releasable for releasing the securement between the tibial resection guide and the upper segment of the alignment shaft, subsequent to affixation of the tibial resection guide to the proximal tibia, and the clamping means of the alignment shaft being selectively releasable for releasing the upper segment of the alignment shaft for movement relative to the lower segment, whereby the tibial resection guide can be independently connected to the upper segment of the alignment shaft while the head is anchored to the proximal tibia and the upper and lower segments of the alignment shaft are clamped together, and can be independently disconnected from the upper segment of the alignment shaft, subsequent to the affixation of the tibial resection guide, to enable withdrawal of the upper segment from the tibial resection guide and provide uninhibited access to the tibial resection guide for accomplishing resection at the selected resection level.

2. The invention of claim 1 wherein the anchoring means includes a first fixation pin for anchoring the head against anterior and posterior movements relative to the tibia, and a second fixation pin for anchoring the head against rotation about the first fixation pin, at least one of the first and second fixation pins being mounted in the head for selective movement in upward and downward directions relative to the head, between an advanced position wherein the moveable fixation pin extends downwardly from the head for extending into the proximal tibia, and a retracted position wherein the moveable fixation pin is retracted from the proximal tibia to enable selective release of the moveable fixation pin from the proximal tibia prior to withdrawal of the upper segment of the alignment shaft from the tibial resection guide to facilitate said withdrawal.

3. The invention of claim 2 wherein the moveable fixation pin is mounted for selective movement independent of the other fixation pin.

4. The invention of claim 2 including mounting means mounting the moveable fixation pin for sliding movement in the head between the advanced position and the retracted position.

5. The invention of claim 1 wherein the anchoring means includes:
- a first fixation pin mounted in the head for selective movement in upward and downward directions relative to the head between an advanced position wherein the first fixation pin extends downwardly from the head for extending into the proximal tibia to anchor the head to the proximal tibia against upward movement of the head, and the upper segment of the alignment shaft, away from the proximal tibia, and a retracted position wherein the first fixation pin is retracted from the proximal tibia to release the head, and the upper segment of the alignment shaft, for upward movement relative to the proximal tibia; and
- a second fixation pin mounted in the head for selective movement in upward and downward directions relative to the head between an advanced position wherein the second fixation pin extends downwardly from the head for extending into the proximal tibia to anchor the head to the proximal tibia against upward movement of the head, and the upper segment of the alignment shaft, away from the proximal tibia, and a retracted position wherein the second fixation pin is retracted from the proximal tibia to release the head, and the upper segment of the alignment shaft, for upward movement relative to the proximal tibia;
- the first and second fixation pins being spaced from one another such that upon movement of both the first and second fixation pins to the respective advanced positions, rotation of the head about one of the first and second pins is precluded; and
- upon movement of both the first and second fixation pins to the respective retracted positions, the fixation pins are retracted from the proximal tibia to enable selective release of the fixation pins from the proximal tibia prior to withdrawal of the upper segment of the alignment shaft from the tibial resection guide to facilitate said withdrawal.

6. The invention of claim 5 wherein the first fixation pin is spaced rearwardly of the alignment axis of the alignment shaft, and the second fixation pin is located between the first fixation pin and the alignment axis of the alignment shaft.

7. The invention of claim 6 wherein the first and second fixation pins are mounted in the head for selective movement independent of one another.

8. The invention of claim 5 including mounting means mounting the first and second fixation pins for sliding movement in the head between the respective advanced positions and retracted positions.

9. The invention of claim 1 wherein the attachment means for attaching the stylus assembly to the tibial resection guide comprises a quick-connect mechanism including an elongate socket extending downwardly into the tibial resection guide, an elongate plug on the stylus assembly, the plug being complementary to the socket and extending in the downward direction, a recess in the tibial resection guide, the recess communicating with the socket and extending transverse to the socket, a projection mounted in the plug for movement in transverse directions between an extended position, wherein the projection engages the recess to secure the plug in the socket, and a retracted position, wherein the projection is released from the recess to release the plug from the socket, and actuator means for selectively moving the projection between the advanced and retracted positions thereof.

10. The invention of claim 9 including biasing means for biasing the actuator means to move the projection into the extended position.

11. An improvement in an apparatus used in connection with the implant of a prosthetic knee implant wherein the proximal tibia of a tibia is prepared for resection for the reception of a tibial component of the prosthetic knee implant, the proximal tibia having a tibial eminence, the improvement comprising:
- an external alignment shaft having an upper end;
- a head at the upper end of the external alignment shaft, the head extending rearwardly for placement over the tibial eminence when the alignment shaft is located forward of the tibia; and
- anchoring means on the head for anchoring the head to the proximal tibia with the alignment shaft located forward of the tibia;
- the anchoring means including a first fixation pin for anchoring the head against anterior and posterior movements relative to the tibia, and a second fixation pin for anchoring the head against rotation about the first fixation pin, and mounting means capturing at least one of the first and second fixation pins in the head for selective movement in upward and downward directions relative to the head, between an advanced position wherein the moveable fixation pin extends downwardly from the head for extending into the proximal tibia, and a retracted position wherein the moveable fixation pin is retracted from the proximal tibia to enable selective release of the moveable fixation pin from the proximal tibia while the head remains in place over the tibial eminence and the moveable fixation pin remains captured in the head.

12. The invention of claim 11 wherein the moveable fixation pin is mounted for selective movement independent of the other fixation pin.

13. The invention of claim 11 wherein the mounting means captures the moveable fixation pin for sliding movement in the head between the advanced position and the retracted position.

14. An improvement in an apparatus used in connection with the implant of a prosthetic knee implant wherein the proximal tibia of a tibia is prepared for resection for the reception of a tibial component of the prosthetic knee implant, the proximal tibia having a tibial eminence, the improvement comprising:
- an external alignment shaft having an upper end;
- a head at the upper end of the external alignment shaft, the head extending rearwardly for placement over the tibial eminence when the alignment shaft is located forward of the tibia; and
- anchoring means on the head for anchoring the head to the proximal tibia with the alignment shaft located forward of the tibia, the anchoring means including:
- a first fixation pin mounted in the head for selective movement in upward and downward directions relative to the head between an advanced position wherein the first fixation pin extends downwardly from the head for extending into the proximal tibia to anchor the head to the proximal tibia against upward movement of the head, and the alignment shaft, away from the proximal tibia, and a retracted position wherein the first fixation pin is retracted from the proximal tibia to release the head, and the alignment shaft, for upward movement relative to the proximal tibia;
- a second fixation pin mounted in the head for selective movement in upward and downward directions relative to the head between an advanced position wherein the second fixation pin extends downwardly from the head for extending into the proximal tibia to anchor the head to the proximal tibia against upward movement of the head, and the alignment shaft, away from the proximal tibia, and a retracted position wherein the second fixation pin is retracted from the proximal tibia to release the head, and the alignment shaft, for upward movement relative to the proximal tibia; and mounting means for capturing the first and second fixation pins within the head;

the first and second fixation pins being spaced from one another such that upon movement of both the first and second fixation pins to the respective advanced positions, rotation of the head about one of the first and second pins is precluded; and upon movement of both the first and second fixation pins to the respective retracted positions, the fixation pins are retracted from the proximal tibia to enable selective release of the fixation pins from the proximal tibia while the head remains in place over the tibial eminence and the first and second fixation pins remain captures in the head.

15. The invention of claim 14 wherein the first fixation pin is spaced rearwardly of the alignment shaft, and the second fixation pin is located between the first fixation pin and the alignment shaft.

16. The invention of claim 15 wherein the first and second fixation pins are mounted in the head for selective movement independent of one another.

17. The invention of claim 15 wherein the mounting means captures the first and second fixation pins for sliding movement in the head between the respective advanced positions and retracted positions.

18. An improvement in a method for implanting a prosthetic knee implant wherein the proximal tibia of a tibia is prepared for resection at a selected resection level for the reception of a tibial component of the prosthetic knee implant, the proximal tibia having a tibial eminence, the improvement comprising the following steps in order:

locating an external alignment shaft having an upper segment and a lower segment, forward of the tibia, the upper segment being selectively movable along an alignment axis relative to the lower segment and having an exposed upper end and a head at the exposed upper end of the upper segment, with the head extending rearwardly relative to the tibia;

placing the head over the tibial eminence when the alignment shaft is located forward of the tibia;

anchoring the head to the proximal tibia with anchoring means, with the alignment shaft located forward of the tibia;

clamping the upper segment and the lower segment of the alignment shaft against movement relative to one another subsequent to anchoring of the head to the proximal tibia;

aligning the alignment shaft relative to the tibia subsequent to anchoring the head to the proximal tibia;

placing a tibial resection guide having coupling means over the exposed upper end of the upper segment of the alignment shaft, from above the exposed upper end, to engage the tibial resection guide with the upper segment and enable movement of the tibial resection guide downwardly, over the exposed upper end, along the upper segment, subsequent to anchoring the head to the proximal tibia;

attaching a stylus assembly to the tibial resection guide for movement with the tibial resection guide along the upper segment, the stylus assembly including a stylus, and engaging the stylus with the proximal tibia to locate the tibial resection guide at a resection location wherein the tibial resection guide is located for resection at the selected resection level;

securing the tibial resection guide against movement along the upper segment when the tibial resection guide is located at the resection location;

affixing the tibial resection guide to the proximal tibia when the tibial resection guide is located at the resection location;

releasing the securement between the tibial resection guide and the upper segment of the alignment shaft, subsequent to affixation of the tibial resection guide to the proximal tibia;

releasing the upper segment of the alignment shaft for movement relative to the lower segment, subsequent to the affixation of the tibial resection guide; and withdrawing the upper segment from the tibial resection guide to provide uninhibited access to the tibial resection guide for accomplishing resection at the selected resection level.

19. The invention of claim 18 wherein the anchoring means includes a first fixation pin for anchoring the head against anterior and posterior movements relative to the tibia, and a second fixation pin for anchoring the head against rotation about the first fixation pin, at least one of the first and second fixation pins being mounted in the head for selective movement in upward and downward directions relative to the head, independent of one another, between an advanced position wherein the moveable fixation pin extends downwardly from the head for extending into the proximal tibia, and a retracted position wherein the moveable fixation pin is retracted from the proximal tibia, the improvement including advancing the first fixation pin into the proximal tibia to first anchor the head to the proximal tibia against anterior and posterior movements relative to the proximal tibia, with the head seated upon the proximal tibia, and subsequently advancing the second fixation pin into the proximal tibia to anchor the head against rotational movement about the first fixation pin.

20. The invention of claim 18 wherein the anchoring means includes a first fixation pin for anchoring the head against anterior and posterior movements relative to the tibia, and a second fixation pin for anchoring the head against rotation about the first fixation pin, the first and second fixation pins being mounted in the head for selective movement in upward and downward directions relative to the head, between an advanced position wherein the fixation pins extend downwardly from the head for extending into the proximal tibia, and a retracted position wherein the fixation pins are retracted from the proximal tibia, the improvement including first seating the head upon the proximal tibia, and then advancing the fixation pins sequentially into the proximal tibia to anchor the head to the proximal tibia.

21. The invention of claim 18 wherein the anchoring means includes a first fixation pin for anchoring the head against anterior and posterior movements relative to the tibia, and a second fixation pin for anchoring the head against rotation about the first fixation pin, at least one of the first and second fixation pins being mounted in the head for selective movement in upward and downward directions relative to the head, between an advanced position wherein the moveable fixation pin extends downwardly from the head for extending into the proximal tibia, and a retracted position wherein the moveable fixation pin is retracted from the proximal tibia, the improvement including releasing the moveable fixation pin from the proximal tibia prior to withdrawal of the upper segment of the alignment shaft from the tibial resection guide to facilitate said withdrawal.

22. The invention of claim 18 wherein the anchoring means includes a first fixation pin mounted in the head for selective movement in upward and downward directions relative to the head between an advanced position wherein the first fixation pin extends downwardly from the head for extending into the proximal tibia to anchor the head to the proximal tibia against upward movement of the head, and the upper segment of the alignment shaft, away from the proximal tibia, and a retracted position wherein the first fixation pin is retracted from the proximal tibia to release the head, and the upper segment of the alignment shaft, for upward movement relative to the proximal tibia, and a second fixation pin mounted in the head for selective movement in upward and downward directions relative to the head between an advanced position wherein the second fixation pin extends downwardly from the head for extending into the proximal tibia to anchor the head to the proximal tibia against upward movement of the head, and the upper segment of the alignment shaft, away from the proximal tibia, and a retracted position wherein the second fixation pin is retracted from the proximal tibia to release the head, and the upper segment of the alignment shaft, for upward movement relative to the proximal tibia, the first and second fixation pins being spaced from one another such that upon movement of both the first and second fixation pins to the respective advanced positions, rotation of the head about one of the first and second pins is precluded, the improvement including retracting the fixation pins from the proximal tibia to release the fixation pins from the proximal tibia prior to withdrawal of the upper segment of the alignment shaft from the tibial resection guide to facilitate said withdrawal without disturbing the affixation of the tibial resection guide on the proximal tibia.

23. The invention of claim 18 wherein the stylus assembly is attached to the tibial resection guide prior to placing the tibial resection guide over the exposed upper end of the upper segment of the alignment shaft to engage the tibial resection guide with the upper segment.

24. An improvement in a method used in connection with the implant of a prosthetic knee implant wherein the proximal tibia of a tibia is prepared for resection at a selected resection level for the reception of a tibial component of the prosthetic knee implant, the proximal tibia having a tibial eminence, the improvement comprising:

locating an external alignment shaft forward of the tibia, the external alignment shaft having an upper end, and a head at the upper end of the external alignment shaft, the head extending rearwardly for placement over the tibial eminence when the alignment shaft is located forward of the tibia; and anchoring the head to the proximal tibia with anchoring means, with the alignment shaft located forward of the tibia, the anchoring means including a first fixation pin for anchoring the head against anterior and posterior movements relative to the tibia, and a second fixation pin for anchoring the head against rotation about the first fixation pin, at least one of the first and second fixation pins being captured in the head for selective movement in upward and downward directions relative to the head, between an advanced position wherein the moveable fixation pin extends downwardly from the head for extending into the proximal tibia, and a retracted position wherein the moveable fixation pin is retracted from the proximal tibia while the movable fixation pin remains captured in the head, the improvement including advancing one of the first and second fixation pins into the proximal tibia to first anchor the head to the proximal tibia against anterior and posterior movements relative to the proximal tibia, with the head seated upon the proximal tibia, and subsequently advancing the other of the first and second fixation pins into the proximal tibia to anchor the head against rotational movement about the said one of the first and second fixation pins.

25. The invention of claim 24 wherein the first fixation pin anchors the head against anterior and posterior movements relative to the tibia, and the second fixation pin anchors the head against rotation about the first fixation pin, each of the first and second fixation pins being mounted in the head for selective movement in upward and downward directions relative to the head, between an advanced position wherein the fixation pins extend downwardly from the head for extending into the proximal tibia, and a retracted position wherein the fixation pins are retracted from the proximal tibia, the improvement including first seating the head upon the proximal tibia, and then advancing the fixation pins sequentially into the proximal tibia to anchor the head to the proximal tibia.

26. The invention of claim 24 including retracting said one of the first and second fixation pins to release said one of the first and second fixation pins from the proximal tibia while maintaining the head seated upon the proximal tibia, and subsequently withdrawing the head from the proximal tibia.

27. The invention of claim 24 wherein the first fixation pin is mounted in the head for selective movement in upward and downward directions relative to the head between an advanced position wherein the first fixation pin extends downwardly from the head for extending into the proximal tibia to anchor the head to the proximal tibia against upward movement of the head, and the alignment shaft, away from the proximal tibia, and a retracted position wherein the first fixation pin is retracted from the proximal tibia to release the head, and the alignment shaft, for upward movement relative to the proximal tibia, and the second fixation pin is mounted in the head for selective movement in upward and downward directions relative to the head between an advanced position wherein the second fixation pin extends downwardly from the head for extending into the proximal tibia to anchor the head to the proximal tibia against upward movement of the head, and the alignment shaft, away from the proximal tibia, and a retracted position wherein the second fixation pin is retracted from the proximal tibia to release the head, and the alignment shaft, for upward movement relative to the proximal tibia, the first and second fixation pins being spaced from one another such that upon movement of both the first and second fixation pins to the respective advanced positions, rotation of the head about one of the first and second pins is precluded, the improvement including retracting the fixation pins from the proximal tibia to release the fixation pins from the proximal tibia while maintaining the head seated upon the proximal tibia, and subsequently withdrawing the head from the proximal tibia.

* * * * *